(12) United States Patent
Lavielle et al.

(10) Patent No.: US 6,239,129 B1
(45) Date of Patent: May 29, 2001

(54) CYANO-INDOLE SEROTONIN-REUPTAKE INHIBITOR COMPOUNDS

(75) Inventors: Gilbert Lavielle, La Celle Saint Cloud; Olivier Muller, Ennery; Bernard Cimetiere, Paris; Mark Millan, Le Pecq; Alain Gobert, Rueil-Malmaison; Jean-Michel Rivet, Nanterre, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/490,909

(22) Filed: Jan. 25, 2000

(30) Foreign Application Priority Data

Jan. 26, 1999 (FR) .................................................. 99 00801

(51) Int. Cl.$^7$ ..................... A61K 31/404; A61K 31/551; A61P 25/28; C07D 243/08; C07D 401/06
(52) U.S. Cl. ..................... 514/218; 514/415; 514/235.2; 514/253; 514/256; 514/259; 514/319; 514/326; 514/339; 514/365; 540/575; 544/143; 544/284; 544/333; 544/373; 546/201; 546/277.1; 548/146; 548/491
(58) Field of Search ..................... 514/415, 253, 514/256; 544/333, 373; 548/491

(56) References Cited

U.S. PATENT DOCUMENTS 5,393,761 * 2/1995 Perregaard et al. ................. 514/323

FOREIGN PATENT DOCUMENTS

814084 A1 * 12/1997 (EP) .

* cited by examiner

Primary Examiner—Jane C. Oswecki
(74) Attorney, Agent, or Firm—The Firm of Heuschen and Sage

(57) ABSTRACT

Compound of formula (I):

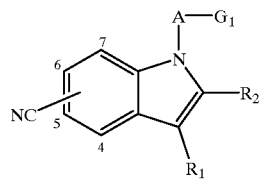

wherein:
  $R_1$ and $R_2$ each independently of the other represents hydrogen or alkyl,
  A represents alkylene, alkenylene or alkynylene,
  $G_1$ represents

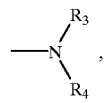

wherein $R_3$ and $R_4$ each independently of the other represents hydrogen, alkyl, cycloalkyl, cycloalkylalkyl, optionally substituted aryl or optionally substituted arylalkyl, or $G_1$ represents heterocycloalkyl optionally substituted by alkyl, cycloalkyl, cycloalkylalkyl, nitrile, carboxy, alkoxycarbonyl, carbamoyl, optionally substituted aryl, optionally substituted arylalkyl, optionally substituted heteroaryl or optionally substituted heteroarylalkyl, and which medicinal products containing the same/are useful as serotonin-reuptake inhibitors.

12 Claims, No Drawings

CYANO-INDOLE SEROTONIN-REUPTAKE INHIBITOR COMPOUNDS

The present invention relates to new cyano-indole serotonin-reuptake inhibitor compounds, to a process for their preparation and to pharmaceutical compositions containing them.

DESCRIPTION OF THE PRIOR ART

Compounds characterised by the combination of an indole ring and a 2,3-dihydro-1,4-benzodioxine ring have been described for their serotonin-reuptake inhibiting properties (WO 9717343). Indoles substituted on the aromatic ring have also been claimed in Application EP 814 084 for their action at the level of the serotonin-reuptake sites. Other compounds having related properties have been claimed in Application WO 9633710 and have a benzopyran structure.

BACKGROUND OF THE INVENTION

Serotonin-reuptake inhibitors constitute a heterogeneous group of therapeutic agents. They are used in the treatment of pathologies associated with a serotonin deficit at the level of the central neurone synapses. The inhibition of serotonin reuptake by binding to transporters or presynaptic receptors is a means of restoring nerve transmission.

The use of compounds having those inhibitory properties may constitute an alternative to the use of tricyclic antidepressants or of monoamine oxidase inhibitors in the treatment of depression and associated disorders (Annals of Pharmacotherapy, 1994, 28, 1359), panic attacks and obsessive-compulsive disorders (Human Psychopharmacology, 1995, 10, 5199). The efficacy of compounds having such pharmacological properties (Journal of Psychopharmacology, 1994, 8, 238) is reinforced by the fact that they are better tolerated (International Clinical Psychopharmacology, 1995, 9 suppl. 4, 33) and are safer to use (Annals of Pharmacology, reference cited).

SUMMARY OF THE INVENTION

The compounds of the present invention are characterised by an indole ring substituted on the aromatic moiety by a cyano group and on the indole nitrogen by an aminoalkyl chain. That novel structure confers upon them in addition of a great affinity for 5-HT$_{2c}$ receptors, a powerful serotonin-reuptake inhibiting character. They will therefore be useful therapeutically in the treatment of depression, panic attacks, obsessive-compulsive disorders, phobias, impulsive disorders associated with drug abuse, bulimia nervosa and anxiety.

DETAILED DESCRIPTION OF THE INVENTION

The present invention relates to compounds of formula (I):

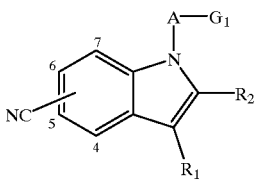

wherein:
  $R_1$ and $R_2$ each independently of the other represents a hydrogen atom or a linear or branched ($C_1$–$C_6$)alkyl group,
  A represents a linear or branched ($C_1$–$C_6$)alkylene group, a linear or branched ($C_2$–$C_6$)-alkenylene group or a linear or branched ($C_2$–$C_6$)alkynylene group,
  $G_1$ represents a grouping

wherein $R_3$ and $R_4$ each independently of the other represents a hydrogen atom, a linear or branched ($C_1$–$C_6$)alkyl group, a ($C_3$–$C_8$)cycloalkyl group, a ($C_3$–$C8$)cycloalkyl-($C_1$–$C_6$)alkyl group in which the alkyl moiety is linear or branched, an optionally substituted aryl group, an optionally substituted aryl-($C_1$–$C_6$)alkyl group in which the alkyl moiety is linear or branched, an optionally substituted heteroaryl group, or an optionally substituted heteroaryl-($C_1$–$C_6$)-alkyl group in which the alkyl moiety is linear or branched,
  or $G_1$ represents a heterocycloalkyl group, bonded to A by any one of the ring junctions and optionally substituted at any one of the ring positions by a linear or branched ($C_1$–$C_6$)alkyl group, a ($C_3$–$C_8$)cycloalkyl group, a ($C_3$–$C_8$)cycloalkyl-($C_1$–$C_6$)alkyl group in which the alkyl moiety is linear or branched, a nitrile group, a carboxy group, a linear or branched ($C_1$–$C_6$)alkoxycarbonyl group, a carbamoyl group (optionally substituted by one or two substituents: linear or branched ($C_1$–$C_6$)alkyl, ($C_3$–$C_8$)cycloalkyl, optionally substituted phenyl and/or optionally substituted benzyl), an optionally substituted aryl group, an optionally substituted aryl-($C_1$–$C_6$)alkyl group in which the alkyl moiety is linear or branched, an optionally substituted heteroaryl group, or an optionally substituted heteroaryl-($C_1$–$C_6$)alkyl group in which the alkyl moiety is linear or branched,
their enantiomers, diastereoisomers, and addition salts thereof with a pharmaceutically acceptable acid or base.

"Heterocycloalkyl group" is understood to mean a saturated cyclic group having from 4 to 8 ring members containing 1 or 2 nitrogen and/or oxygen atoms. There may be mentioned more especially the groups piperidine, piperazine, 1,4-diazepan, pyrrolidine and morpholine, etc.

"Aryl" is understood to mean a group selected from phenyl and naphthyl.

"Heteroaryl group" is understood to mean a monocyclic or polycyclic, unsaturated or partially unsaturated, group having from 4 to 22 ring members and containing from 1 to 10 hetero atoms selected from nitrogen, oxygen and sulphur.

The expression "optionally substituted" applied to the terms "phenyl", "benzyl", "aryl", "arylalkyl", "heteroaryl" and "heteroarylalkyl" means that the groups in question are substituted on their cyclic moiety by one or more halogen atoms and/or linear or branched ($C_1$–$C_6$)alkyl groups, linear or branched ($C_1$–$C_6$)alkoxy groups, hydroxy groups, perhalo-($C_1$–$C_6$)alkyl groups in which the alkyl moiety is linear or branched, amino groups (optionally substituted by one or two linear or branched ($C_1$–$C_6$)alkyl groups), and/or nitro groups, it being understood that the heteroaryl and heteroarylalkyl groups can also be substituted by an oxo group.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned by way of non-limiting example sodium hydroxide, potassium hydroxide, triethylamine, tert-butylamine., etc.

Advantageously, the invention relates to compounds of formula (I) wherein the cyano group is attached in the 5-position of the indole group.

Another advantageous aspect of the invention relates to compounds of formula (I) wherein the cyano group is attached in the 6-position of the indole group.

In the compounds of formula (I), preferably $R_1$ and $R_2$ each represents a hydrogen atom.

The preferred compounds of formula (I) are those wherein A represents a linear or branched ($C_1$–$C_6$)alkylene group.

In the preferred compounds of formula (I), $G_1$ represents a grouping

wherein $R_3$ and $R_4$ are preferably selected from a hydrogen atom, a linear or branched ($C_1$–$C_6$)alkyl group, an aryl group and an aryl-($C_1$–$C_6$)alkyl group in which the alkyl moiety is linear or branched.

In other preferred compounds of the invention, $G_1$ represents an optionally substituted heterocycloalkyl group.

The preferred heterocycloalkyl groups are the groups piperazine, 1,4-diazepan, pyrrolidine (3-pyrrolidinyl) and piperidine. Those groups are advantageously substituted by a group selected from aryl (for example phenyl) which is optionally substituted, aryl-($C_1$–$C_6$)allyl in which the alkyl moiety is linear or branched (for example benzyl, phenethyl or phenylpropyl) which is optionally substituted, and heteroaryl (for example piperazine, pyridine, 2-oxo-2,3-dihydro-1H-indole, 5-oxo-5H-[1,3]thiazolo[3,2-a ] pyrimidine, or 2,4-dioxo-1,4-dihydro-3-(2H)-quinazoline), which is optionally substituted.

An especially advantageous aspect of the invention relates to compounds of formula (I) wherein the cyano group is attached in the 5- or 6-position of the indole group, $R_1$ and $R_2$ each represents a hydrogen atom, A represents a linear or branched ($C_1$–$C_6$)alkylene group, and $G_1$ represents a grouping

wherein $R_3$ and $R_4$ are each independently of the other selected from a hydrogen atom, a linear or branched ($C_1$–$C_6$) alkyl group, an aryl group and an aryl-($C_1$–$C_6$)alkyl group in which the alkyl moiety is linear or branched, or $G_1$ represents an optionally substituted heterocycloalkyl group selected from piperazine, pyrrolidine (3-pyrrolidinyl), piperidine and 1,4-diazepan.

Among the preferred compounds of the invention, there may be mentioned more especially:
- 1-{3-[4-(5-methoxy-4-pyrimidinyl)-1-piperazinyl] propyl}-1H-indole-6-carbonitrile,
- 1-{[1-(2-chlorophenethyl)-3-pyrrolidinyl]methyl}-1H-indole-6-carbonitrile,
- 1-[3-(dimethylamino)propyl]-1H-indole-6-carbonitrile.

The invention relates also to a process for the preparation of compounds of formula (I), characterised in that there is used as starting material a compound of formula (II):

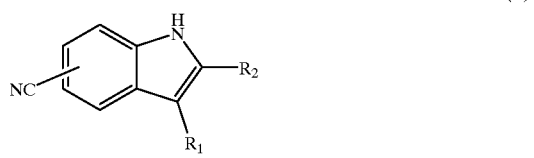

(II)

wherein $R_1$ and $R_2$ are as defined for formula (I), which, after treatment in a basic medium, may be subjected to:
→ the action of a compound of formula (III):

P—A—$G_1$ (III)

wherein A and $G_1$ are as defined for formula (I), and P represents a leaving group (for example a tosyl group), to yield a compound of formula (I),
or
→ mthe action of a compound of formula (IV):

Hal—A—OH (IV)

wherein A is as defined for formula (I), and Hal represents a halogen atom,
to yield a compound of formula (V):

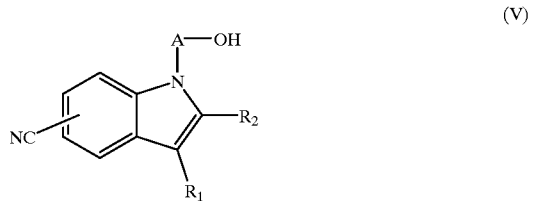

(V)

wherein $R_1$, $R_2$ and A are as defined hereinbefore, which, after bromination of the hydroxyl finction, or conversion of the latter to a leaving group, is subjected, in a basic medium, to the action of a compound of formula (VI):

$G_1$—H (VI)

wherein $G_1$ is as defined for formula (I),
to yield a compound of formula (I), it being understood that the grouping $G_1$, when it represents an amino group or an unsubstituted heterocycloalkyl group, may be substituted in a final step, in order to introduce substituents as defined for formula (I), using conventional reactions of organic chemistry,
which compound of formula (I):

- may be purified, if necessary, according to a conventional purification technique,
- is separated, where appropriate, into its isomers according to a conventional separation technique,
- is converted, if desired, into addition salts thereof with a pharmaceutically acceptable acid or base.

The present invention relates also to pharmaceutical compositions comprising as active ingredient at least one compound of formula (I) on its own or in combination with one or more inert, non-toxic pharmaceutically acceptable excipients or carriers.

Among the pharmaceutical compositions according to the invention there may be mentioned more especially those that are suitable for oral, parenteral or nasal administration, tablets or dragees, sublingual tablets, gelatin capsules, lozenges, suppositories, creams, ointments, dermal gels, etc.

The useful dosage varies according to the age and weight of the patient, the nature and severity of the disorder and the route of administration, which may be oral, nasal, rectal or parenteral. The unit dose generally ranges from 0.1 to 500 mg for a treatment in from 1 to 3 administrations per 24 hours.

The following Examples illustrate the invention and do not limit it in any way.

The starting materials used are known products or are prepared according to known procedures.

EXAMPLE 1

1-{3-[4-(5-Methoxy-4-pyrimidinyl)-1-piperazinyl] propyl}-1H-indole-6-carbonitrile dihydrochloride Step a: 1-(3-Hydroxypropyl)-1H-indole-6-carbonitrile 0.776 mol (87 g) of potassium tert-butylate is added to a solution of 0.703 mol (100 g) of 6-cyanoindole in 2500 ml of tetrahydrofluran at 20° C. After 15 minutes' stirring, 1.41 mol (196 g) of 3-bromo-1-propanol are added and the reaction mixture is stirred for 24 hours at room temperature. After concentration, the residue is taken up in 1000 ml of dichloromethane, and the organic phase is washed with 500 ml of water an d then with 500 ml of a saturated sodium chloride solution. The organic phase is then dried and concentrated to yield the expected compound.

Step b: 1-(3-Bromopropyl)-1H-6-carbonitrile

A solution of 0.78 mol (204 g) of triphenyiphosphine in 600 ml of acetonitrile is added at 20° C. to a solution of 0.7 mol (140 g) of the compound described in the preceding Step and 0.85 mol (280 g) of tetrabromomethane in 2000 ml of acetonitrile. After 4 hours' stirring, the reaction mixture is purified by chromatography over silica gel using a cyclohexane/ethyl acetate mixture, 90/10, as eluant to yield the expected product.

Step c: 1-{3-[4-(5-Methoxy-4-pyrimidinyl)-1-piperazinyl] propyl}-1H-indole-6-carbonitrile dihydrochloride A mixture of 11.4 mmol (3 g) of the compound described in the preceding Step, 12.5 mmol (2.43 g) of 5-methoxy-4-(1-piperazinyl)pyrimidirie and 1.3 g of sodium carbonate in 60 ml of acetonitrile is heated at reflux for 3 hours. After cooling and concentration, the residue is taken up in 100 ml of dichloromethane, and the organic phase is washed with water, driede and concentrated. The resulting residue is purified by chromatography over silica gel using a dichloromethane/methanol/ammonia mixture, 90/10/1, as eluant. The corresponding dihydrochloride is obtained by the action of a titrated solution of HCl in ethanol.

Melting point: 178–180° C.

Elemental micro analysis:

|  | C | H | N | Cl |
|---|---|---|---|---|
| % calculated | 56.12 | 5.84 | 18.71 | 15.78 |
| % found | 56.85 | 6.04 | 18.70 | 14.98 |

EXAMPLE 2

1-[3-(Dimethylamino)propyl]-1H-indole-6-carbonitrile hydrochloride

A mixture of 11.4 mmol (3 g) of the compound described in Step b of Example 1 and 22.8 mmol (2.6 g) of an aqueous 40% dimethylamine solution in 60 ml of acetonitrile is heated at 70° C. for 1 hour. After cooling, the reaction mixture is concentrated, and the resulting residue is taken up in 100 ml of dichloromethane. The organic phase is washed with water, dried and concentrated to yield the expected product. The corresponding hydrochloride is obtained by the action of a titrated solution of HCl in ethanol.

Melting point: 168–170° C.

Elemental micro analysis:

|  | C | H | N | Cl |
|---|---|---|---|---|
| % calculated | 63.75 | 6.88 | 15.93 | 13.44 |
| % found | 62.90 | 6.88 | 15.50 | 12.39 |

EXAMPLE 3

1-{3-[Benzyl(methyl)amino]propyl}-1H-indole-6-carbonitrile

The expected product is obtained according to the process described in Step c of Example 1, replacing 5-methoxy-4-(1-piperazinyl)pyrimidine by N-methylbenzylamine.

Melting point: 68–70° C.

Elemental micro analysis:

|  | C | H | N | Cl |
|---|---|---|---|---|
| % calculated | 70.68 | 6.52 | 12.36 | 10.43 |
| % found | 70.43 | 6.54 | 12.17 | 10.55 |

EXAMPLE 4

1-(3-Pyrrolidinylmethyl)-1H-indole-6-carbonitrile hydrochloride

Step a: Tert-butyl 3-[(6-cyano-1H-indol-1-yl)methyl]-1-pyrrolidinecarboxylate 77 mmol of potassium tert-butylate are added to a solution of 70 mmol of 6-cyanoindole in 400 ml of tetrahydrofuran. After 10 minutes' stirring at room temperature, 70 mmol of tert-butyl 3-[(methylphenyl)sulphonyloxymethyl]-1-pyrrolidinecarboxylate in 60 ml of tetrahydrofuran are added. The reaction mixture is heated at reflux for 12 hours. After cooling and dilution with water, the solvent is removed by evaporation. The residue is extracted with dichloromethane and the organic phase is washed with water, dried and concentrated to yield the expected product.

Step b: 1-(3-Pyrrolidinylmethyl)-1H-indole-6-carbonitrile hydrochloride 40 ml of trifluoroacetic acid are added to a solution of 70 mmol of the compound described in the preceding Step in 290 ml of dichloromethane. The reaction mixture is stirred at room temperature for 2h30. After removal of solvent by evaporation, the residue is taken up in dichloromethane and washed with a 1M sodium carbonate solution. The organic phase is dried, concentrated and purified by chromatography over silica gel using a dichloromethane/methanol/ammonia mixture, 85/15/1, as eluant to yield the expected product. The corresponding hydrochloride is obtained by the action of a titrated solution of HCl in ethanol.

Elemental microanalysis:

|  | C | H | N | Cl |
|---|---|---|---|---|
| % calculated | 64.24 | 6.16 | 16.05 | 13.54 |
| % found | 64.35 | 6.40 | 15.96 | 13.67 |

EXAMPLE 5

1-[(1-Benzyl-3-pyrrolidinyl)methyl]1H-indole-6-carbonitrile hydrochloride 4.4 mmol of potassium carbonate and then 4.4 mmol of benzyl bromide are added to a solution of 4.4 mmol of the compound described in Example 4 in 20 ml of acetonitriie. After stirring at reflux for 2h30, the reaction mixture is cooled and diluted with a dichloromethane/water mixture. The organic phase is separated off, dried and concentrated. The resulting residue is purified by chromatography over silica gel using an ethyl acetate/cyclohexane mixture, 50/50, as eluant to yield the expected product. The corresponding hydrochloride is obtained by the action of a titrated solution of HCl in ethanol.

Elemental microanalysis:

|  | C | H | N | Cl |
|---|---|---|---|---|
| % calculated | 71.68 | 6.30 | 11.64 | 10.08 |
| % found | 71.40 | 6.38 | 11.65 | 10.05 |

EXAMPLE 6

1-{[1-(3-Chlorobenzyl)-3-pyrrolidinyl]methyl}-1H-indole-6-carbonitrile hydrochloride The expected product is obtained according to the process described in Example 5, replacing benzyl bromide by 3-chlorobenzyl bromide.

Elemental microanalysis:

|  | C | H | N | Cl |
|---|---|---|---|---|
| % calculated | 65.29 | 5.48 | 10.88 | 9.18 |
| % found | 65.16 | 5.54 | 10.72 | 9.04 |

EXAMPLE 7

1-[(1-Phenethyl-3-pyrrolidinyl)methyl]-1H-indole-6-carbonitrile hydrochloride

The expected product is obtained according to the process described in Example 5, replacing benzyl bromide by phenethyl bromide.

Elemental microanalysis:

|  | C | H | N | Cl |
|---|---|---|---|---|
| % calculated | 72.22 | 6.61 | 11.48 | 9.69 |
| % found | 71.88 | 6.68 | 11.45 | 9.74 |

EXAMPLE 8

1-{[1-(2-Chlorobenzyl)-3-pyrrolidinyl]methyl}-1H-indole-6-carbonitrile hydrochloride The expected product is obtained according to the process described in Example 5, replacing benzyl bromide by 2-chlorobenzyl bromide.

Elemental microanalysis:

|  | C | H | N | Cl |
|---|---|---|---|---|
| % calculated | 65.29 | 5.48 | 10.88 | 9.18 |
| % found | 65.42 | 5.58 | 10.78 | 9.03 |

EXAMPLE 9

1-(3-Pyrrolidinylmethyl)-1H-indole-5-carbonitrile hydrochloride

The expected product is obtained according to the process described in Example 4, replacing 6-cyanoindole by 5-cyanoindole.

Elemental microanalysis:

|  | C | H | N | Cl |
|---|---|---|---|---|
| % calculated | 62.24 | 6.16 | 16.05 | 13.54 |
| % found | 64.10 | 6.10 | 15.86 | 13.68 |

EXAMPLE 10

1-[(1-Benzyl-3-pyrrolidinyl)methyl]-1H-indole-5-carbonitrile hydrochloride

The expected product is obtained according to the process described in Example 5, replacing the compound of Example 4 by the compound described in Example 9.

EXAMPLE 11

1-{[1-(3-Chlorobenzyl)-3-pyrrolidinyl]methyl}-1H-indole-5-carbonitrile hydrochloride The expected product is obtained according to the process described in Example 5, replacing the compound of Example 4 by the compound described in Example 9, and replacing benzyl bromide by 3-chlorobenzyl bromide.

Elemental microanalysis:

|  | C | H | N | Cl |
|---|---|---|---|---|
| % calculated | 65.29 | 5.48 | 10.88 | 9.18 |
| % found | 65.45 | 5.47 | 10.61 | 9.29 |

EXAMPLE 12

1-[(1-Phenethyl-3-pyrrolidinyl)methyl]-1H-indole-5-carbonitrile hydrochloride

The expected product is obtained according to the process described in Example 5, replacing the compound of Example 4 by the compound described in Example 9, and replacing benzyl bromide by phenethyl bromide.

Elemental microanalysis:

|  | C | H | N | Cl |
|---|---|---|---|---|
| % calculated | 72.22 | 6.61 | 11.48 | 9.69 |
| % found | 72.22 | 6.75 | 11.20 | 9.61 |

EXAMPLE 13

1-{[1-(2-Chlorobenzyl)-3-pyrrolidinyl]methyl}-1H-indole-5-carbonitrile hydrochloride The expected product is obtained according to the process described in Example 5, replacing the compound of Example 4 by the compound described in Example 9, and replacing benzyl bromide by 2-chlorobenzyl bromide.

Elemental micro analysis:

|  | C | H | N | Cl |
|---|---|---|---|---|
| % calculated | 65.29 | 5.48 | 10.88 | 9.18 |
| % found | 65.78 | 5.57 | 10.64 | 9.16 |

EXAMPLE 14

1-(3-{4-[4-(Trifluoromethyl)-2-pyridinyl]-1-piperazinyl}propyl)-1H-indole-6-carbonitrile dihydrochloride The expected product is obtained according to the process described in Example 1, replacing 5-methoxy-4-(1-piperazinyl)pyrimidine by 4-trifluoromethyl-2-(1-piperazinyl)-pyridine in Step c.

Elemental microanalysis:

|  | C | H | N | Cl |
|---|---|---|---|---|
| % calculated | 54.33 | 4.97 | 14.40 | 14.45 |
| % found | 54.33 | 5.04 | 14.10 | 14.20 |

EXAMPLE 15

1-{3-[4-(5-Methoxy-4-pyrimidinyl)-1,4-diazepan-1-yl]propyl}-1H-indole-6-carbonitrile dihydrochloride The expected product is obtained according to the process described in Example 1, replacing 5-methoxy-4-(1-piperazinyl)pyrimidine by 4-(1,4-diazepan-1-yl)-5-methoxypyrimidine in Step c.

Elemental microanalysis:

|  | C | H | N | Cl |
|---|---|---|---|---|
| % calculated | 57.02 | 6.09 | 18.14 | 15.30 |
| % found | 57.39 | 6.23 | 17.86 | 15.07 |

EXAMPLE 16

1-{3-[4-(2-Methoxyphenyl)-1-piperazinyl]propyl)-1H-indole-6-carbonitrile dihydrochloride The expected product is obtained according to the process described in Example 1, replacing 5-methoxy-4-(1-piperazinyl)pyrimidine by 1-(2-methoxyphenyl)piperazine in Step c.

Elemental microanalysis:

|  | C | H | N | Cl |
|---|---|---|---|---|
| % calculated | 61.75 | 6.31 | 12.52 | 15.85 |
| % found | 61.50 | 6.24 | 12.20 | 15.54 |

EXAMPLE 17

1-{[1-(3-Phenylpropyl)-3-pyrrolidinyl]methyl}-1H-indole-6-carbonitrile hydrochloride The expected product is obtained according to the process described in Example 5, replacing benzyl bromide by 1-(3-bromopropyl)benzene.

Elemental microanalysis:

|  | C | H | N | Cl |
|---|---|---|---|---|
| % calculated | 72.71 | 6.90 | 11.06 | 9.33 |
| % found | 72.67 | 6.99 | 10.92 | 9.56 |

EXAMPLE 18

1-{[1-(3-Phenylpropyl)-3-pyrrolidinyl]methyl}-1H-indole-5-carbonitrile hydrochloride The expected product is obtained according to the process described in Example 5, replacing the compound of Example 4 by the compound described in Example 9 and replacing benzyl bromide by 1-(3-bromopropyl)benzene.

Elemental microanalysis:

|  | C | H | N | Cl |
|---|---|---|---|---|
| % calculated | 72.71 | 6.90 | 10.06 | 9.33 |
| % found | 72.48 | 6.91 | 10.84 | 9.21 |

EXAMPLE 19

1-({1-[2-(1-Naphthyl)ethyl]-3-pyrrolidinyl}methyl)-1H-indole-6-carbonitrile hydrochloride The expected product is obtained according to the process described in Example 5, replacing benzyl bromide by 1-(2-bromoethyl)naphthalene.

Elemental microanalysis:

|  | C | H | N | Cl |
|---|---|---|---|---|
| % calculated | 75.08 | 6.30 | 10.10 | 8.52 |
| % found | 74.67 | 6.36 | 9.82 | 8.57 |

EXAMPLE 20

1-{[1-(3-Chlorophenethyl)-3-pyrrolidinyl]methyl}-1H-indole-6-carbonitrile hydrochloride The expected product is obtained according to the process described in Example 5, replacing benzyl bromide by 1-(2-bromoethyl)-3-chlorobenzene.

Elemental microanalysis:

|  | C | H | N | Cl |
|---|---|---|---|---|
| % calculated | 66.00 | 5.79 | 10.50 | 17.71 |
| % found | 66.25 | 5.98 | 10.20 | 17.53 |

EXAMPLE 21

1-{[1-(4-Methoxyphenethyl)-3-pyrrolidinyl]methyl}-1H-indole6-carbonitrile hydrochloride The expected product is obtained according to the process described in Example 5, replacing benzyl bromide by 1-(2-bromoethyl)-4-methoxybenzene.

Elemental microanalysis:

|  | C | H | N | Cl |
|---|---|---|---|---|
| % calculated | 69.77 | 6.62 | 10.61 | 8.95 |
| % found | 69.64 | 6.44 | 10.36 | 8.98 |

EXAMPLE 22

1-{[1-(3-Fluorophenethyl)-3-pyrrolidinyl]methyl}-1H-indole-6-carbonitrile hydrochloride The expected product is obtained according to the process described in Example 5, replacing benzyl bromide by 1-(2-bromoethyl)-3-fluorobenzene.

Elemental microanalysis:

|  | C | H | N | Cl |
|---|---|---|---|---|
| % calculated | 68.83 | 6.04 | 10.95 | 9.24 |
| % found | 68.24 | 5.98 | 10.55 | 9.46 |

EXAMPLE 23

1-({1-[2-(2-Naphthyl)ethyl]-3-pyrrolidinyl}methyl)-1H-indole-6-carbonitrile hydrochloride The expected product is obtained according to the process described in Example 5, replacing benzyl bromide by 2-(2-bromoethyl)naphthalene.

Elemental microanalysis:

|  | C | H | N | Cl |
|---|---|---|---|---|
| % calculated | 75.08 | 6.30 | 10.10 | 8.52 |
| % found | 74.75 | 6.43 | 9.81 | 9.03 |

EXAMPLE 24

1-{[1-(2-Chlorophenethyl)-3-pyrrolidinyl]methyl}-1H-indole-6-carbonitrile hydrochloride The expected product is obtained according to the process described in Example 5, replacing benzyl bromide by 1-(2-bromoethyl)-2-chlorobenzene.

Elemental microanalysis:

|  | C | H | N | Cl |
|---|---|---|---|---|
| % calculated | 66.00 | 5.79 | 10.50 | 17.71 |
| % found | 66.98 | 5.95 | 10.43 | 17.58 |

EXAMPLE 25

1-{[1-(4-Fluorophenethyl)-3-pyrrolidinyl]methyl}-1H-indole-6-carbonitrile hydrochloride The expected product is obtained according to the process described in Example 5, replacing benzyl bromide by 1-(2-bromoethyl)-4-fluorobenzene.

Elemental microanalysis:

|  | C | H | N | Cl |
|---|---|---|---|---|
| % calculated | 68.83 | 6.04 | 10.95 | 9.24 |
| % found | 68.93 | 6.10 | 10.48 | 8.96 |

EXAMPLE 26

1-({1-[2-(6-Chloro-2-oxo-2,3-dihydro-1H-indol-5-yl)ethyl]-3-pyrrolidinyl}methyl)-1H-indole-6-carbonitrile hydrochloride The expected product is obtained according to the process described in Example 5, replacing benzyl bromide by 6-chloro-5-(2-chloroethyl)-1,3-dihydro-indol-2-one.

Elemental microanalysis:

|  | C | H | N | Cl |
|---|---|---|---|---|
| % calculated | 63.30 | 5.31 | 12.30 | 15.57 |
| % found | 63.68 | 5.54 | 11.58 | 14.88 |

EXAMPLE 27

1-({1-[2-(7-Methyl-5-oxo-5H-[1,3]thiazolo[3,2-a]pyrimidin-6-yl)ethyl]-3-pyrrolidinyl}methyl)-1H-indole-6-carbonitrile hydrochloride The expected product is obtained according to the process described in Example 5, replacing benzyl bromide by 6-(2-chloroethyl)-7-methyl-[1,3]thiazolo[3,2-a]pyrimidin-5-one.

Elemental microanalysis:

|  | C | H | N | Cl |
|---|---|---|---|---|
| % calculated | 60.85 | 5.33 | 15.43 | 7.06 |
| % found | 59.23 | 5.63 | 14.16 | 6.56 |

EXAMPLE 28

1-({1-[2-(2,4-Dioxo-1,4-dihydro-3-(2H)-quinazolinyl)ethyl]-3-pyrrolidinyl}methyl)-1H-indole-6-carbonitrile hydrochloride The expected product is obtained according to the process described in Example 5, replacing benzyl bromide by 3-(2-chloroethyl)-(1H)-quinazoline-2,4-dione.

Elemental microanalysis:

|  | C | H | N | Cl |
|---|---|---|---|---|
| % calculated | 64.07 | 5.38 | 15.57 | 7.88 |
| % found | 63.56 | 5.56 | 14.58 | 7.82 |

EXAMPLE 29

1-{3-[Cyclohexyl(methyl)amino]propyl}-1H-indole-6-carbonitrile

The expected product is obtained according to the process described in Example 1, Step c, replacing 5-methoxy-4-(1-piperazinyl)pyrimidine by N-methylcyclohexylamine.

EXAMPLE 30

1-[3-(Benzylamino)propyl]-1H-indole-6-carbonitrile

The expected product is obtained according to the process described in Example 1, Step c, replacing 5-methoxy-4-(1-piperazinyl)pyrimidine by N-benzylamine.

EXAMPLE 31

1-{3-[Phenyl(methyl)amino]propyl}-1H-indole-6-carbonitrile

The expected product is obtained according to the process described in Example 1, Step c, replacing 5-methoxy-4-(1-piperazinyl)pyrrolidine by N-methylaniline.

EXAMPLE 32

1-(3-{[2-(1-Piperidinyl)ethyl]amino}propyl)-1H-indole-6-carbonitrile

The expected product is obtained according to the process described in Example 1, Step c, replacing 5-methoxy-4-(1-piperazinyl)pyrimidine by N-(2-aminoethyl)piperidine.

EXAMPLE 33

1-(3-{[2-(1-Pyrrolidinyl)ethyl]amino}propyl)-1H-indole-6-carbonitrile

The expected product is obtained according to the process described in Example 1, Step c, replacing 5-methoxy-4-(1-piperazinyl)pyrimidine by N-(2-aminoethyl)pyrrolidine.

EXAMPLE 34

1-[3-(4-Morpholinyl)propyl]-1H-indole-6-carbonitrile

The expected product is obtained according to the process described in Example 1, Step c, replacing 5-methoxy-4-(1-piperazinyl)pyrimidine by morpholine.

EXAMPLE 35

1-{2-[4-(5-Methoxy-4-pyrimidinyl)-1-piperazinyl]ethyl}-1H-indole-6-carbonitrile dihydrochloride The expected product is obtained according to the process described in Example 1, replacing 3-bromo-1-propanol by 2-bromo-1-ethanol in Step a.

EXAMPLE 36

1-{2-[4-(2-Methoxyphenyl-1-piperazinyl]ethyl)-1H-indole-6-carbonitrile dihydrochloride The expected product is obtained according to the process described in Example 1, replacing 3-bromo-1-propanol by 2-bromo-1-ethanol in Step a, and replacing 5-methoxy-4-(1-piperazinyl)pyrimidine by 1-(2-methoxyphenyl)piperazine in Step c.

PHARMACOLOGICAL STUDY

Example A
Determination of Affinity for Serotonin-reuptake Sites in the Rat

The affinity of the compounds of the invention was determined by competition experiments with [$^3$H]-paroxetine. The membranes are prepared from rat frontal cortex and are incubated in triplicate with 0.25 nM [$^3$H]-paroxetine and the cold ligand in a final volume of 0.4 ml, for 2 hours at 25° C. The incubation buffer contains 50 mM TRIS-HCl (pH 7.4), 120 mM NaCl and 5 mM KCl. Non-specific binding is determined using 10 μM citalopram. At the end of the incubation, the mixture is filtered through filters and washed three times with 5 ml of cooled buffer. The radioactivity retained on the filters is determined by liquid scintillation counting. The binding isotherms are analysed by non-linear regression to determine the IC$_{50}$ values. The latter are converted into a dissociation constant (K$_i$) using the Cheng-Prusoff equation:

$$K_i = IC_{50} / \{(L/K_d) - 1\}$$

wherein L is the concentration of [$^3$H]-paroxetine and K$_d$ is the dissociation constant (0.13 nM).

The compounds of the invention appear to have a very high affinity for serotonin-reuptake sites.

By way of example, the compound of Example 1 has a dissociation constant $K_i$ of $9.8 \times 10^{-9}$ M.

Example B
Determination of Affinity for $5\text{-HT}_{2c}$ Receptors

The affinity of the compounds of the invention was determined by competition experiments with [³H]-mesulergine, in an incubation buffer Hepes 20 mM, EDTA 2 mM, ascorbic acid 0.1% (pH=7.7) at 22° C. The dissociation constant $K_D$ of [³H]-mesulergine is 0.54 mM. Non specific binding is determined using 1 μM mianserine, also reference product for each experiment.

At the end of the incubation, the mixture is filtered through filters GF/B-Unifilter (treated with PEI (0.1%)), and washed three times with the incubation buffer.

The radioactivity retained on the filters is determined by liquid scintillation counting. The binding isotherms are analysed by non-linear regression to determine the $IC_{50}$ values. The latter are converted into a dissociation constant $K_i$.

The compounds of the invention appear to have a very high affinity for $5\text{-HT}_{2c}$ receptors, their dissociation constant being in a range of $10^{-8}$ to $10^{-9}$ M.

Example C
Pharmaceutical Composition

| Formulation for the preparation of 1000 tablets each comprising a dose of 10 mg: | |
| --- | --- |
| Compound of Example 1 | 10 g |
| Hydroxypropyl cellulose | 2 g |
| Wheat starch | 10 g |
| Lactose | 100 g |
| Magnesium stearate | 3 g |
| Talc | 3 g |

We claim:
1. A compound selected from those of formula (I):

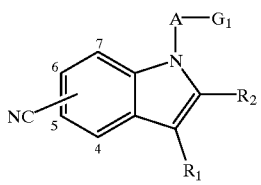

(I)

wherein:
$R_1$ and $R_2$ each independently of the other represents hydrogen, or linear or branched ($C_1$–$C_6$)alkyl,
A represents linear or branched ($C_1$–$C_6$)alkylene, linear or branched ($C_2$–$C_6$)-alkenylene, or linear or branched ($C_2$–$C_6$)alkynylene,
$G_1$ represents

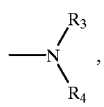

wherein $R_3$ and $R_4$ each independently of the other represents hydrogen, linear or branched ($C_1$–$C_6$)alkyl, ($C_3$–$C_8$) cycloalkyl, ($C_3$–$C_8$)cycloalkyl-($C_1$–$C_6$)alkyl in which the alkyl moiety is linear or branched, optionally substituted aryl, optionally substituted aryl-($C_1$–$C_6$)alkyl in which the alkyl moiety is linear or branched, optionally substituted heteroaryl, or optionally substituted heteroaryl-($C_1$–$C_6$)-alkyl in which the alkyl moiety is linear or branched, or $G_1$ represents heterocycloalkyl, bonded to A by any one of the ring junctions and optionally substituted at any one of the ring positions by linear or branched ($C_1$–$C_6$) alkyl, ($C_3$–$C_8$)cycloalkyl, ($C_3$–$C_8$)cycloalkyl-($C_1$–$C_6$) alkyl in which the alkyl moiety is linear or branched, nitrile, carboxy, linear or branched ($C_1$–$C_6$)alkoxycarbonyl, carbamoyl optionally substituted by one or two substituents selected from linear or branched ($C_1$–$C_6$)alkyl, ($C_3$–$C_8$)cycloalkyl, optionally substituted phenyl and/or optionally substituted benzyl, optionally substituted aryl, optionally substituted aryl-($C_1$–$C_6$)alkyl in which the alkyl moiety is linear or branched, optionally substituted heteroaryl, or optionally substituted heteroaryl-($C_1$–$C_6$)alkyl in which the alkyl moiety is linear or branched, its enantiomers, diastereoisomers, and addition salts thereof with a pharmaceutically-acceptable acid or base.

2. A compound of claim 1 wherein the cyano group is attached in the 6-position of the indole group.

3. A compound of claim 1 wherein the cyano group is attached in the 5-position of the indole group.

4. A compound of claim 1 wherein A represents linear or branched ($C_1$–$C_6$)alkylene.

5. A compound of claim 1 wherein $G_1$ represents

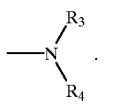

6. A compound of claim 1 wherein $G_1$ represents optionally substituted heterocycloalkyl.

7. A compound of claim 1 wherein the cyano group is attached in the 5- or 6-position of the indole group, $R_1$ and $R_2$ each represents hydrogen, A represents linear or branched ($C_1$–$C_6$)alkylene, and $G_1$ represents

wherein $R_3$ and $R_4$ are each independently of the other selected from hydrogen, linear or branched ($C_1$–$C_6$)alkyl, aryl and aryl-($C_1$–$C_6$)alkyl in which the alkyl moiety is linear or branched, or $G_1$ represents optionally substituted heterocycloalkyl selected from piperazine pyrrolidine, piperidine and 1,4-diazepan, addition salts thereof with a pharmaceutically-acceptable acid or base.

8. A compound of claim 1 which is selected from 1-{3-[4-(5-methoxy-4-pyrimidinyl)-1-piperazinyl]propyl}-1H-indole-6-carbonitrile dihydrochloride, and its addition salts with a pharmaceutically-acceptable acid.

9. A compound of claim 1 which is selected from 1-[3-(dimethylamino)propyl]-1H-indole-6-carbonitrile hydrochloride, and its addition salts with a pharmaceutically-acceptable acid.

10. A compound of claim 1 which is selected from 1-{[1-(2-chlorophenethyl)-3-pyrrolidinyl]methyl}-1H-indole-6-carbonitrile, and its addition salts with a pharmaceutically-acceptable acid.

11. A method for treating a living body afflicted with a condition requiring a serotonin-reuptake inhibitor selected from depression, obsessive-compulsive disorders, phobias, impulsive disorders associated with drug abuse, bulimia nervosa, and anxiety, comprising the step of administering to the living body an amount of a compound of claim 1 which is effective for alleviation of said condition.

12. A pharmaceutical composition useful as serotonin-reuptake inhibitor, comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 6,239,129 B1
DATED : May 29, 2001
INVENTOR(S) : Gilbert Lavielle et al.

It is certified that error appears in the above-identified patent and that said Letters Patent is hereby corrected as shown below:

<u>Column 16,</u>
Line 54 and 55, change the comma after "diazepan" to a period and delete the remainder of the line which reads (addition salts thereof with a pharmaceutically-acceptable acid or base.)

Signed and Sealed this

Twelfth Day of February, 2002

Attest:

JAMES E. ROGAN
*Attesting Officer*  *Director of the United States Patent and Trademark Office*